United States Patent
Ho et al.

(10) Patent No.: US 11,717,546 B2
(45) Date of Patent: *Aug. 8, 2023

(54) COMPOSITION FOR PROMOTING DEFECATION AND USE THEREFOR

(71) Applicant: GLAC BIOTECH CO., LTD, Tainan (TW)

(72) Inventors: Hsieh-Hsun Ho, Tainan (TW); Ching-Wei Chen, Tainan (TW); Yi-Wei Kuo, Tainan (TW); Yu-Fen Huang, Tainan (TW); Jui-Fen Chen, Tainan (TW); Cheng-Chi Lin, Tainan (TW)

(73) Assignee: GLAC BIOTECH CO., LTD, Tainan (TW)

(*) Notice: Subject to any disclaimer, the term of this patent is extended or adjusted under 35 U.S.C. 154(b) by 0 days.

This patent is subject to a terminal disclaimer.

(21) Appl. No.: 17/246,977

(22) Filed: May 3, 2021

(65) Prior Publication Data
US 2021/0401908 A1    Dec. 30, 2021

(30) Foreign Application Priority Data

Jun. 29, 2020   (TW) .................................. 109121775

(51) Int. Cl.
| | | |
|---|---|---|
| *A61K 35/747* | (2015.01) | |
| *A61P 1/10* | (2006.01) | |
| *A23L 33/135* | (2016.01) | |
| *A61K 35/745* | (2015.01) | |
| *A61K 35/744* | (2015.01) | |
| *A23C 9/123* | (2006.01) | |

(52) U.S. Cl.
CPC .......... *A61K 35/747* (2013.01); *A23C 9/1234* (2013.01); *A23L 33/135* (2016.08); *A61K 35/744* (2013.01); *A61K 35/745* (2013.01); *A61P 1/10* (2018.01)

(58) Field of Classification Search
None
See application file for complete search history.

(56) References Cited

FOREIGN PATENT DOCUMENTS

WO    WO-2007140621 A1 * 12/2007 ............. A23C 9/123

OTHER PUBLICATIONS

MamiBuy. https://mamibuy.com.tw/talk/article/108013 (accessed Jun. 27, 2022). English Machine Translation. (Year: 2019).*

(Continued)

*Primary Examiner* — Michelle F. Paguio Frising
*Assistant Examiner* — Grant C Currens
(74) *Attorney, Agent, or Firm* — Locke Lord LLP; Tim Tingkang Xia, Esq.

(57) ABSTRACT

The present invention provides a method for promoting defecation, comprising administering a composition which includes: a fermentation powder of lactic acid bacteria and a physiologically acceptable excipient, diluent, or carrier. The fermentation powder includes: a fermentation product of lactic acid bacteria, the fermentation product is obtained by incubating lactic acid bacterial strains in a culture medium containing milk, milk powders, casein, soy beans, bean products, or whey, and the lactic acid bacterial strains include: a *Lactobacillus salivarius* subsp. *salicinius* AP-32 strain, a *Lactobacillus plantarum* LPL28 strain, a *Lactobacillus acidophilus* TYCA06 strain, and a *Bifidobacterium longum* subsp. *infantis* BLI-02 strain.

10 Claims, 3 Drawing Sheets

(56) References Cited

OTHER PUBLICATIONS

NCT03228563. "The Effect of Probiotics on Chronic Kidney Disease". https://clinicaltrials.gov/ct2/show/NCT03228563 (accessed Jun. 27, 2022). (Year: 2017).*

Song, D. et al. "Recent Application of Probiotics in Food and Agricultural Science" In "Probiotics", Chapter 1; IntechOpen: London, UK; pp. 3-36. (Year: 2012).*

Rajilic-Stojanovic, et al. "The first 1000 cultured species of the human gastrointestinal microbiota", FEMS Microbiology Reviews, vol. 38, pp. 996-1047. (Year: 2014).*

Ikee et al. "Constipation in chronic kidney disease: it is time to reconsider", Renal Replacement Therapy, vol. 5(51). pp. 1-10. (Year: 2019).*

* cited by examiner

COMPOSITION FOR PROMOTING DEFECATION AND USE THEREFOR

CROSS REFERENCE

This non-provisional application claims priority of Taiwan Invention Patent Application No. 109121775, filed on Jun. 29, 2020, the contents thereof are incorporated by reference herein.

FIELD OF THE INVENTION

The present invention is directed to a composition, and more particularly to a composition for promoting defecation and use therefor.

BACKGROUND OF THE INVENTION

Constipation is a symptom that the formation of hard dry stools and the difficulty in defecating lead to a decrease in the defecating frequency or a decrease in the stool output. Usually, constipation results from a decrease in the large intestine motility and the subsequent delay of the stool passing through the large intestine and out of the rectum. When stools overstay in the rectum, bacteria can overly decompose food in the large intestine to produce toxin or toxic gas; if the stools don't pass out of the body on time, the body can absorb these toxic substances and these toxic substances can flow into blood to harm the body and to lead to chronic diseases or metabolic diseases.

Most over-the-counter drugs for the treatment of constipation, such as laxatives or stool softeners, can bear side effects upon use and increase the addictive potential upon long-term use. That is, these over-the-counter drugs are harmful to health in the long term.

According to the paper published in The American Journal of Clinical Nutrition, Volume 100, Issue 4, October 2014, Pages 1075-1084, probiotics can aid the maintenance of intestinal balance, and improve the intestinal transit time for food, the defecating frequency, and the stool consistency. Therefore, chronically taking probiotics can improve constipation. Probiotics are live bacteria helpful to human. However, if probiotics adhere to or colonize in the intestine in an insufficient amount, the efficiency for maintaining intestinal balance and improving constipation can diminish.

As above, it is desirable to develop a supplement for promoting defecation, which is safe to human and able to be chronically taken. The fermentation product of lactic acid bacteria is safer to the human body than most over-the-counter drugs for the treatment of constipation and is able to be rapidly adsorbed by human. Therefore, there is a need for those skilled in this art to look for a fermentation product of lactic acid bacteria which can increase the defecation efficiency and be manufactured as a composition for improving constipation.

SUMMARY OF THE INVENTION

An objective of the present invention is to provide a fermentation powder of lactic acid bacteria for promoting defecation, which can lead to an increase in the defecating frequency, and thus be manufactured as a food composition or a pharmaceutical composition for improving constipation.

Therefore, the present invention provides a composition for promoting defecation, which comprises: a fermentation powder of lactic acid bacteria and a physiologically acceptable excipient, diluent, or carrier; wherein the fermentation powder comprises: a fermentation product of lactic acid bacteria, the fermentation product is obtained by incubating lactic acid bacterial strains in a culture medium containing milk, milk powders, casein, soy beans, bean products, or whey, and the lactic acid bacterial strains comprise: a *Lactobacillus salivarius* subsp. *salicinius* AP-32 strain, a *Lactobacillus plantarum* LPL28 strain, a *Lactobacillus acidophilus* TYCA06 strain, and a *Bifidobacterium longum* subsp. *infantis* BLI-02 strain; wherein the *Lactobacillus salivarius* subsp. *salicinius* AP-32 strain is deposited at the China Center for Type Culture Collection under an accession number CCTCC M2011127, the *Lactobacillus plantarum* LPL28 strain is deposited at the China General Microbiological Culture Collection Center under an accession number CGMCC 17954, the *Lactobacillus acidophilus* TYCA06 strain is deposited at the China General Microbiological Culture Collection Center under an accession number CGMCC 15210, and the *Bifidobacterium longum* subsp. *infantis* BLI-02 strain is deposited at the China General Microbiological Culture Collection Center under an accession number CGMCC 15212.

Preferably, the lactic acid bacterial strains are consisted of the *Lactobacillus salivarius* subsp. *salicinius* AP-32 strain, the *Lactobacillus plantarum* LPL28 strain, the *Lactobacillus acidophilus* TYCA06 strain, and the *Bifidobacterium longum* subsp. *infantis* BLI-02 strain.

Preferably, the composition is a food composition or a pharmaceutical composition, but not limited thereto.

Preferably, while the composition is a pharmaceutical composition, the physiologically acceptable excipient, diluent, or carrier is a pharmaceutically acceptable excipient, diluent, or carrier, but not limited thereto.

Preferably, the pharmaceutical composition is in tablet form, capsule form, powder form, cream form, spray form, gel form, solution form, or dispersant form, but not limited thereto.

Preferably, while the composition is a food composition, the physiologically acceptable excipient, diluent, or carrier is an edibly acceptable excipient, diluent, or carrier, but not limited thereto.

Preferably, the food composition is fermented milk drink, yogurt, cheese, powders of a milk product, tea, coffee, or energy drink, but not limited thereto.

Preferably, based on the total weight of the composition, the fermentation product is present in 2-40 wt. %.

Preferably, the fermentation product is a fermented supernatant of the culture medium, a fermented supernatant of the culture medium containing inactivated strains, a fermented supernatant of the culture medium free of strains, or a powder thereof, but not limited thereto.

Preferably, the composition further comprises: prebiotics.

According to that the composition can promote defecation in the human body or the animal body, the present invention also provides a method for improving constipation by administering the composition to a subject in need thereof.

Preferably, a symptom of the constipation comprises: formation of hard dry stools, a decrease in stool amount, difficulty in defecating, feeling incomplete bowel movement, or a decrease in defecating frequency.

DETAILED DESCRIPTION OF THE INVENTION

Figure 1:
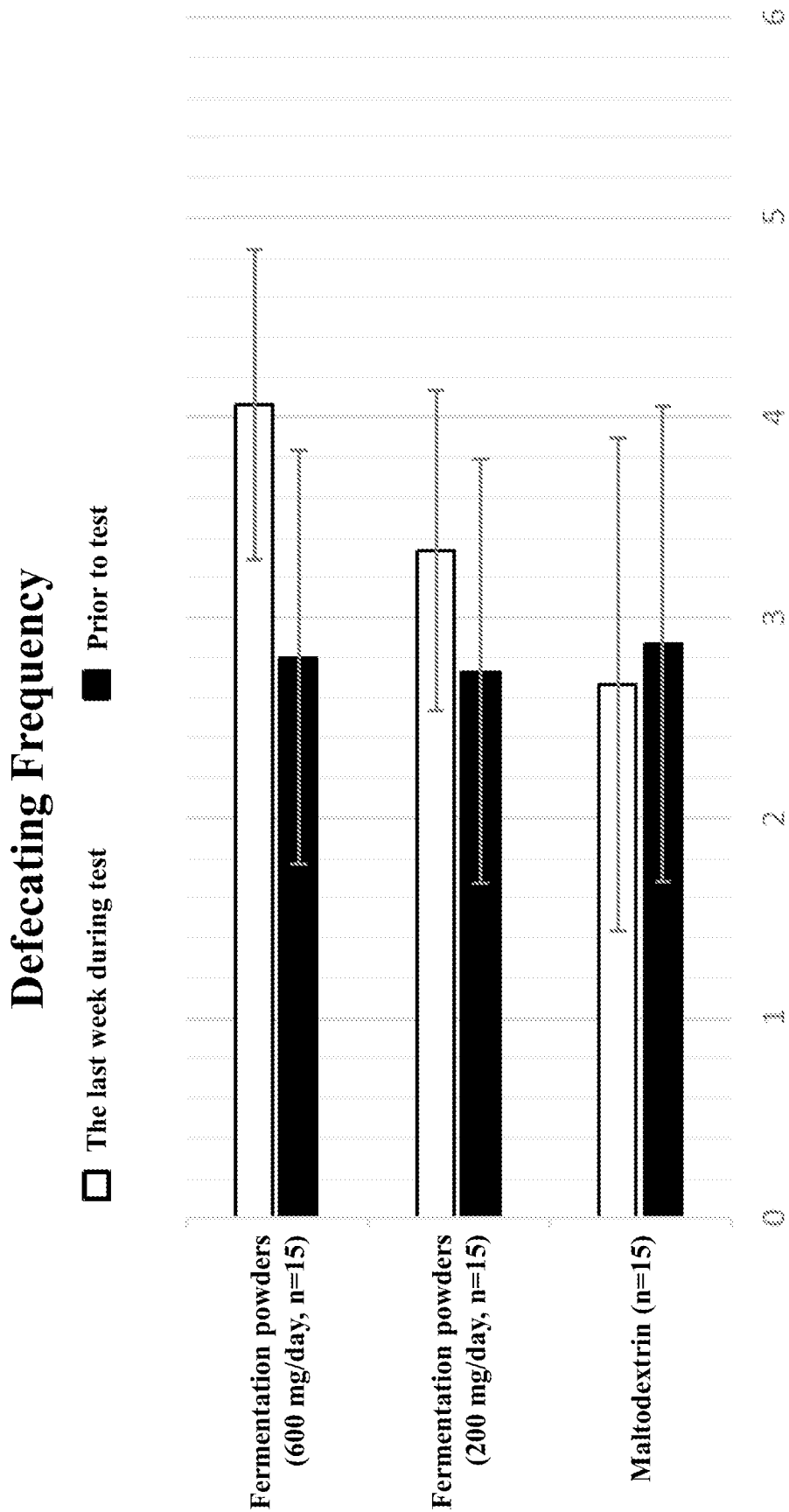
FIG. 1 is a bar graph illustrating the defecating frequency of different subjects.

The detailed description and preferred embodiments of the invention will be set forth in the following content, and provided for people skilled in the art to understand the characteristics of the invention.

The freeze-dried culture of each lactic acid bacterial strain according to the present invention is deposited at the China Center for Type Culture Collection in Wuhan University, Wuhan City, China or deposited at the China General Microbiological Culture Collection Center in No. 3, No. 1 Courtyard, Beichen West Road, Chaoyang District, Beijing City, China. The deposition information is listed in Table 1 below.

TABLE 1

Deposition information of lactic acid bacterial strains

| Strain | Classification | Accession number | Deposition date |
| --- | --- | --- | --- |
| AP-32 | Lactobacillus salivarius subsp. salicinius | CCTCC M2011127 | Apr. 10, 2011 |
| LPL28 | Lactobacillus plantarum | CGMCC 17954 | Jun. 18, 2019 |
| TYCA06 | Lactobacillus acidophilus | CGMCC 15210 | Jan. 15, 2018 |
| BLI-02 | Bifidobacterium longum subsp. infantis | CGMCC 15212 | Jan. 15, 2018 |

The inventors discover that the fermentation product of the strains as shown in Table 1 had an effect on an increase in defecating frequency. Accordingly, the fermentation product can be produced in powder form to be a composition for improving constipation.

An embodiment of the present invention discloses a composition for promoting defecation, and the composition comprises a fermentation powder of lactic acid bacteria and a physiologically acceptable excipient, diluent, or carrier. The fermentation powder includes a fermentation product of lactic acid bacteria, the fermentation product is obtained by incubating lactic acid bacterial strains in a culture medium containing milk, milk powders, casein, soy beans, bean products, or whey, and the lactic acid bacterial strains comprise: a *Lactobacillus salivarius* subsp. *salicinius* AP-32 strain, which is deposited at the China Center for Type Culture Collection under an accession number CCTCC M2011127, a *Lactobacillus plantarum* LPL28 strain, which is deposited at the China General Microbiological Culture Collection Center under an accession number CGMCC 17954, a *Lactobacillus acidophilus* TYCA06 strain, which is deposited at the China General Microbiological Culture Collection Center under an accession number CGMCC 15210, and a *Bifidobacterium longum* subsp. *infantis* BLI-02 strain, which is deposited at the China General Microbiological Culture Collection Center under an accession number CGMCC 15212. In an example, based on the total weight of the composition, the fermentation product of lactic acid bacteria is present in an amount of 2-40 wt. %. In an example, the fermentation product is a fermented supernatant of the culture medium, a fermented supernatant of the culture medium containing inactivated strains, a fermented supernatant of the culture medium free of strains, or a powder thereof. In an example, the lactic acid bacterial strains are consisted of the above-mentioned four kinds of bacterial strains.

In order to meet actual requirements, the composition is a food composition or a pharmaceutical composition. On the condition of a pharmaceutical composition, the physiologically acceptable excipient, diluent, or carrier is a pharmaceutically acceptable excipient, diluent, or carrier, and the pharmaceutical composition is in tablet form, capsule form, powder form, cream form, spray form, gel form, solution form, or dispersant form; on the condition of a food composition, the physiologically acceptable excipient, diluent, or carrier is an edibly acceptable excipient, diluent, or carrier, and the food composition is fermented milk drink, yogurt, cheese, powders of a milk product, tea, coffee, or energy drink. Additionally, in order to assist the growth of probiotics in the gastrointestinal tract, the composition optionally comprises: prebiotics. By the use of prebiotics, the gastrointestinal health can enhance so as to enhance the defecation-promoting function of the composition.

According to the function of the foregoing composition, another embodiment of the present invention discloses a method for improving constipation, and the method comprises the step of: administering the composition to a subject in need thereof. Additionally, a symptom of the constipation comprises: formation of hard dry stools, a decrease in stool amount, difficulty in defecating, feeling incomplete bowel movement, or a decrease in defecating frequency.

Example 1

Morphological and Common Properties of Lactic Acid Bacterial Strains

The 16S ribosomal RNA (rRNA) sequencing and the API bacterial identification system were used to identify the morphological properties of bacterial strains. The morphological properties and common properties of the bacterial strains used in this example are listed in Table 2 below.

TABLE 2

Morphological and common properties of lactic acid bacterial strains

| Strains | Properties |
| --- | --- |
| Lactobacillus salivarius subsp. salicinius AP-32 strain | 1. They are gram-positive and non-sporogenous bacteria without catalase and oxidase and without mobility. They can survive in an aerobic environment or an anaerobic environment, and the most suitable temperature for survival is 37 ± 1° C. They are facultative heterofermentative bacteria and can't produce any gas during glucose metabolism.<br>2. Their colony formed on a MRS agar medium is in the form of white solid circle. Their |

TABLE 2-continued

Morphological and common properties of lactic acid bacterial strains

| Strains | Properties |
| --- | --- |
| | bodies are in the shape of short rod, and tails thereof are in the form of circle. They usually appear alone. |
| *Lactobacillus plantarum* LPL28 strain | 1. They are gram-positive and non-sporogenous bacteria without catalase and oxidase and without mobility. They can survive in an aerobic environment or an anaerobic environment, and the most suitable temperature for survival is 37 ± 1° C. They are facultative heterofermentative bacteria and can't produce any gas during glucose metabolism.<br>2. Their colony formed on a MRS agar medium is in the form of white solid circle. Their bodies are in the shape of short rod, and tails thereof are in the form of square. They usually appear in pairs or arrange in short chains. |
| *Lactobacillus acidophilus* TYCA06 strain | 1. They are gram-positive and non-sporogenous bacteria without catalase and oxidase and without mobility. They can survive in an aerobic environment or an anaerobic environment, and the most suitable temperature for survival is 37 ± 1° C. They are facultative heterofermentative bacteria and can't produce any gas during glucose metabolism.<br>2. Their colony formed on a MRS agar medium is in the translucent irregular form. Their bodies are in the shape of medium rod, and tails thereof are in the form of circle. They usually appear in pairs or arrange in short chains. |
| *Bifidobacterium longum* subsp. *infantis* BLI-02 strain | 1. They are anaerobes and gram-positive and non-sporogenous bacteria without catalase and oxidase and without mobility. They can survive in a strict anaerobic environment, and the most suitable temperature for survival is 37 ± 1° C. They are facultative heterofermentative bacteria and can't produce any gas during glucose metabolism.<br>2. Their colony formed on a MRS agar medium is in the form of white solid circle. Their bodies are in the shape of medium rod or long rod, and two ends thereof are often in the form of branch, e.g. the Y-shaped form or the V-shaped form. |

Example 2

Production of Fermentation Powders of Lactic Acid Bacteria

Isolated *Lactobacillus salivarius* subsp. *salicinius* AP-32 strains, *Lactobacillus plantarum* LPL28 strains, *Lactobacillus acidophilus* TYCA06 strains, and *Bifidobacterium longum* subsp. *infantis* BLI-02 strains were incubated in a culture medium containing milk, milk powders, casein, soy beans, bean products, or whey for fermentation. Then, centrifugation was performed on the culture medium to obtain a fermentation liquid. After which, the fermentation liquid was treated to inactivate the strains therein by heat sterilization, to filter out the strains therein, or to form dried powders by drying. Finally, the dried powders were used as the fermentation powders of lactic acid bacteria as described in this example, or the fermentation liquid containing the inactivated strains or the fermentation liquid without the strains was additionally treated to form the fermentation powders of lactic acid bacteria as described in this example.

Example 3

Defecation Test

In this example, the effect of fermentation powders of lactic acid bacteria as described above on human defecation was determined. Firstly, 200 g of fermentation powders of lactic acid bacteria was mixed with 300 g of maltodextrin to form a capsule. In another aspect, 500 g of maltodextrin was manufactured to form another capsule as reference. Next, 45 volunteer subjects were divided into three groups, each group containing 15 subjects, and then every subject's defecation frequency per week prior to test was recorded. Afterward, one group of the subjects took the reference capsule merely containing maltodextrin every day in consecutive 30 days, another group of the subjects took one capsule containing 200 g of fermentation powders every day in consecutive 30 days, and the other group of the subjects took three capsules every day in consecutive 30 days, each capsule containing 200 g of fermentation powders. Finally, every subject's defecation frequency in the last week during test was recorded.

As shown in FIG. 1, the defecation frequency of the subjects taking the reference capsule every day does not increase, which indicates maltodextrin can't promote defecation. The defecation frequency of the subjects taking 200 g of fermentation powders every day slightly increases, and the defecation frequency of the subjects taking 600 g of fermentation powders every day significantly increases. As above, it is proven that the fermentation powders have effect on promoting defecation.

Example 4

Test for the Apparent Comfort Level of Gastrointestinal Health

In this example, the effect of fermentation powders of lactic acid bacteria as described above on the human's apparent comfort level of gastrointestinal health was determined. Firstly, 200 g of fermentation powders of lactic acid bacteria was mixed with 300 g of maltodextrin to form a capsule. In another aspect, 500 g of maltodextrin was manufactured to form another capsule as reference. Next, 15 volunteer subjects were divided into three groups, each containing 5 subjects. Each group of the subjects took the following substances for a period in a randomized sequence: one reference capsule, one capsule containing 200 g of fermentation powders, and three capsules each containing 200 g of fermentation powders. The interval between taking two different substances was one week, and the improvement level of constipation, flatulence, diarrhea, epigastralgia, and hypogastralgia during taking the same substance was recorded as the apparent comfort score.

Figure 2:
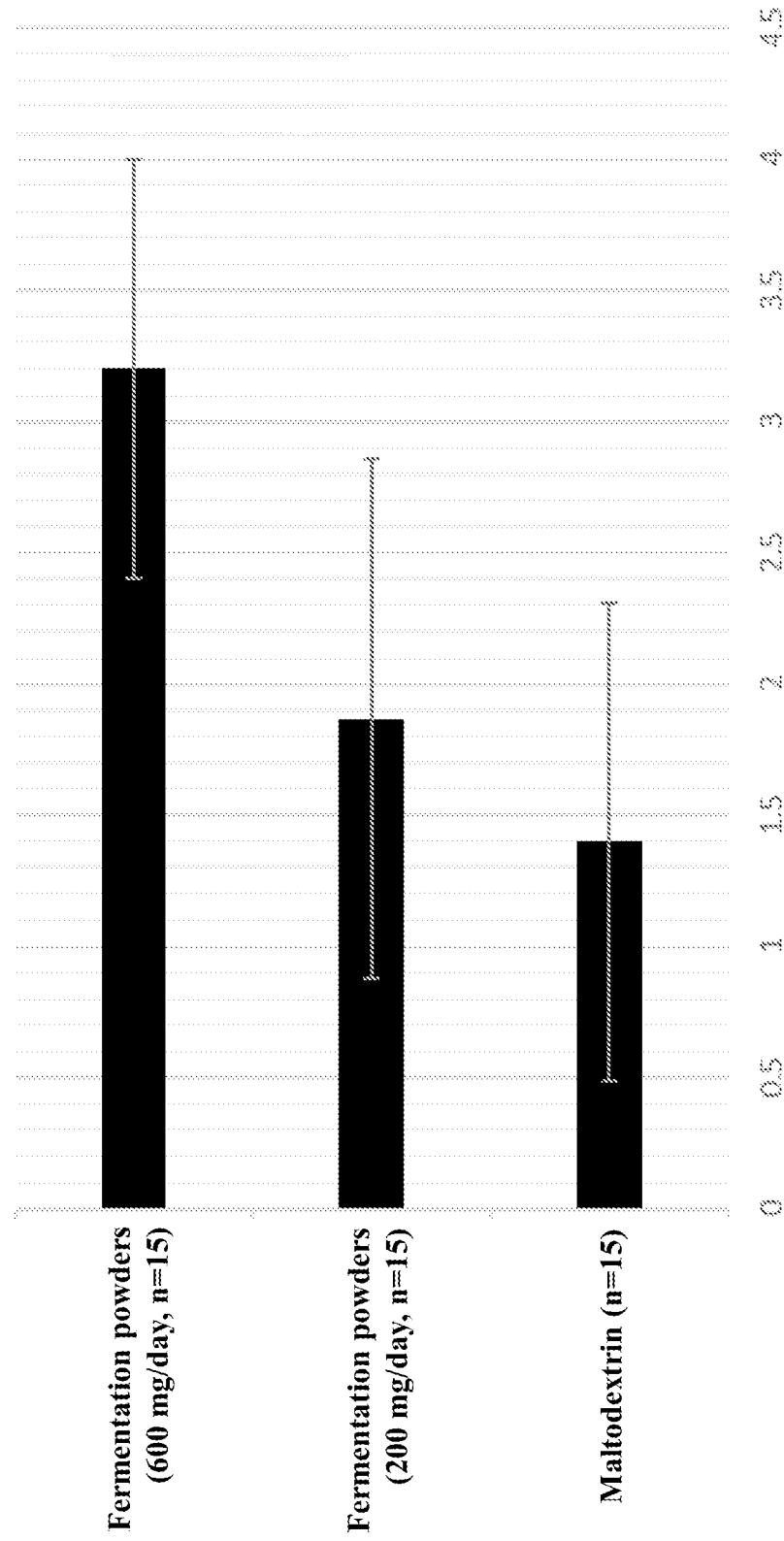
FIG. 2 is a bar graph illustrating the apparent comfort level of gastrointestinal health after the subjects taking different substances.

As shown in FIG. 2, the subjects do not have a feeling of the gastrointestinal health improvement after taking the reference capsule; the subjects have a slight feeling of the gastrointestinal health improvement after taking 200 g of fermentation powders; the subjects have a significant feeling of the gastrointestinal health improvement after taking 600 g of fermentation powders. As above, it is proven that the fermentation powders have effect on increasing the apparent comfort level of gastrointestinal health.

Example 5

Test for Gastrointestinal Microflora

In this example, the effect of fermentation powders of lactic acid bacteria as described above on the gastrointestinal microflora was determined. Firstly, 200 g of fermentation powders of lactic acid bacteria was mixed with 300 g of maltodextrin to form a capsule. In another aspect, 500 g of maltodextrin was manufactured to form another capsule as reference. Next, 45 volunteer subjects were divided into three groups, each containing 15 subjects, and then every subject's stool sample prior to test was obtained. Afterward, one group of the subjects took the reference capsule merely containing maltodextrin every day in consecutive 30 days, another group of the subjects took one capsule containing 200 g of fermentation powders every day in consecutive 30 days, and the other group of the subjects took three capsules every day in consecutive 30 days, each capsule containing 200 g of fermentation powders. Every subject's stool sample after test was obtained. Finally, the next generation sequencing (NGS) was performed to detect the stool microflora.

Figure 3:
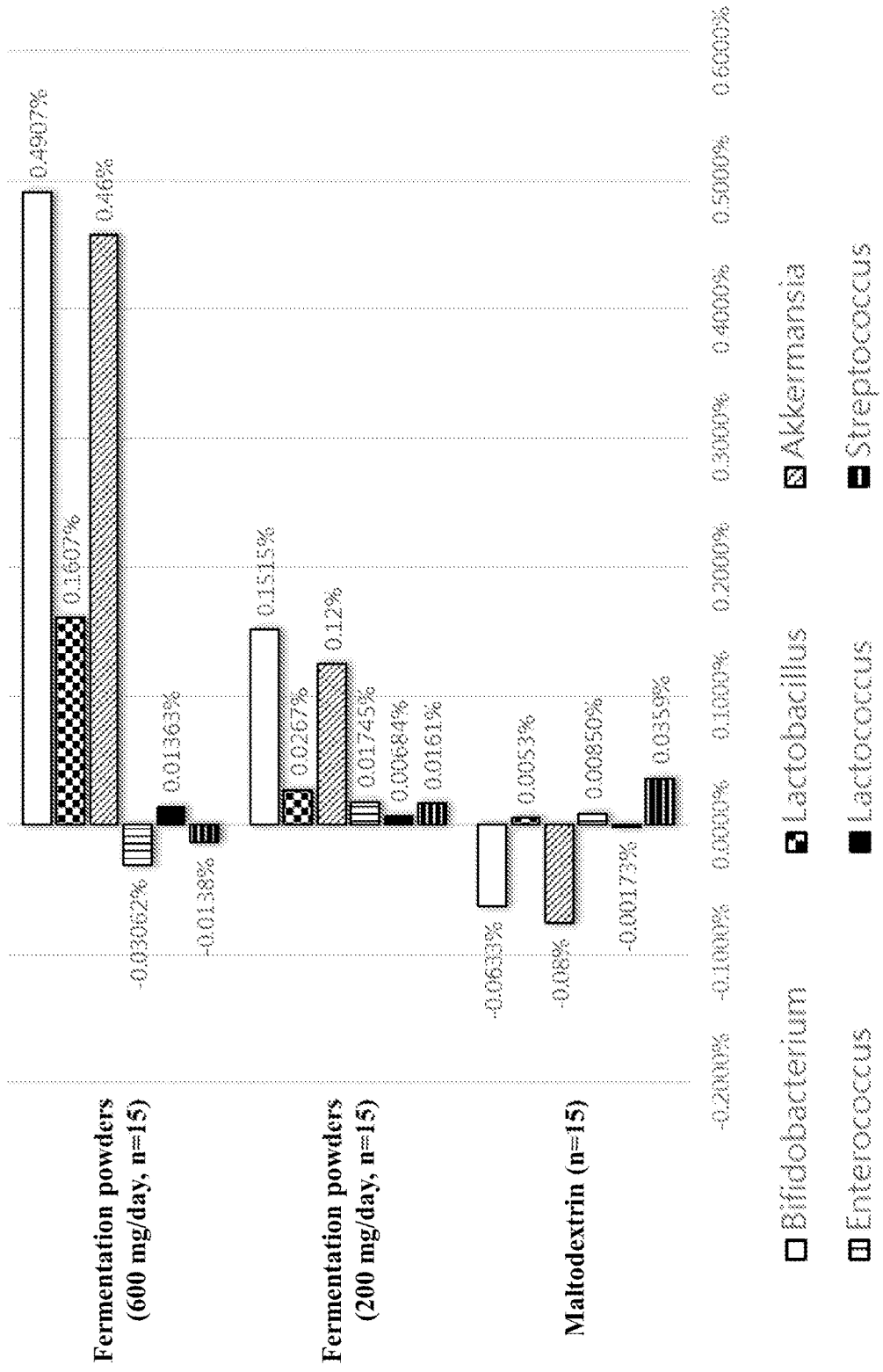
FIG. 3 is a bar graph illustrating the microflora change of different subjects.

*Bifidobacterium*, *Akkermansia*, *Lactococcus*, and *Lactobacillus* belong to beneficial bacteria, and *Enterococcus* and *Streptococcus* belong to pathogenic bacteria. As shown in FIG. 3, in the subject taking the reference capsule, the flora of pathogenic bacteria slightly increases and that of beneficial bacteria slightly decrease; in the subject taking 200 g of fermentation powders, the flora of pathogenic bacteria and that of beneficial bacteria both slightly increase; in the subject taking 600 g of fermentation powders, the flora of pathogenic bacteria significantly decreases and that of beneficial bacteria significantly increases.

Example 6

Test for the Water Content in a Stool

In this example, the effect of fermentation powders of lactic acid bacteria as described above on the water content in a constipated mouse's stool was determined. Firstly, 7 or 8-week-old Balb/c mice were fed or injected with an antidiarrheal agent, loperamide hydrochloride, to establish the animal model of constipation. Then, these constipated mice were divided into the following groups: (1) a reference group; (2) a group for fermentation powders of *Lactobacillus salivarius* subsp. *salicinius* AP-32 strains; (3) a group for fermentation powders of *Lactobacillus plantarum* LPL28 strains; (4) a group for fermentation powders of *Lactobacillus acidophilus* TYCA06 strains; (5) a group for fermentation powders of *Bifidobacterium longum* subsp. *infantis* BLI-02 strains; (6) a mixed fermentation product group; and (7) a mixed strain group. The term "mixed fermentation product" indicated that fermentation powders of lactic acid bacteria as described above; the term "mixed strain" indicated that a combination of *Lactobacillus salivarius* subsp. *salicinius* AP-32 strains, *Lactobacillus plantarum* LPL28 strains, *Lactobacillus acidophilus* TYCA06 strains, and *Bifidobacterium longum* subsp. *infantis* BLI-02 strains. After which, feeding was performed, and 0.25 mL of normal saline was used as a solvent during feeding. Feeding was performed twice daily in consecutive 8 days. In the reference group, the mice were merely fed with normal saline every time; in the group for fermentation powders of *Lactobacillus salivarius* subsp. *salicinius* AP-32 strains, the group for fermentation powders of *Lactobacillus plantarum* LPL28 strains, the group for fermentation powders of *Lactobacillus acidophilus* TYCA06 strains, and the group for fermentation powders of *Bifidobacterium longum* subsp. *infantis* BLI-02 strains, the mice were fed with 600 mg of fermentation powders of the corresponding bacterial strains every time; in the mixed fermentation product group, the mice were fed with 600 mg of fermentation powders of lactic acid bacteria as described above every time and the fermentation powders of a single species of the strains weighed 150 mg; in the mixed strain group, the mice were fed with $2\times10^{10}$ cfu of the total strains every time, and a single species of the strains accounted for $5\times10^9$ cfu. Finally, stool samples were obtained and the water content of each sample was calculated according to the following formula:

$$\text{Stool water content}(\%) = \frac{\text{Stool wet weight} - \text{Stool dry weight}}{\text{Stool wet weight}} \times 100\%$$

The result of the stool water content is shown in Table 3 below.

TABLE 3

| | Stool water content | |
|---|---|---|
| | Stool water content (%) | Increment of stool water content (%) |
| Reference group | 0.38 ± 0.150 | 0 |
| Group for fermentation powders of *Lactobacillus salivarius* subsp. salicinius AP-32 strains | 0.60 ± 0.126 | 0.22 |
| Group for fermentation powders of *Lactobacillus plantarum* LPL28 strains | 0.54 ± 0.093 | 0.16 |
| Group for fermentation powders of *Lactobacillus acidophilus* TYCA06 strains | 0.61 ± 0.076 | 0.23 |
| Group for fermentation powders of *Bifidobacterium longum* subsp. *infantis* BLI-02 strains | 0.57 ± 0.150 | 0.19 |
| Mixed fermentation product group | 0.68 ± 0.096 | 0.30 |
| Mixed strain group | 0.52 ± 0.103 | 0.14 |

As shown above, the increase (0.30%) in the stool water content by feeding the mixed fermentation products is higher than the average (0.2%) of the total increases in the stool water content by merely feeding the fermentation powders of *Lactobacillus salivarius* subsp. *salicinius* AP-32 strains, by merely feeding the fermentation powders of *Lactobacillus acidophilus* TYCA06 strains, by merely feeding the fermentation powders of *Lactobacillus acidophilus* TYCA06 strains, and by feeding the fermentation powders of *Bifidobacterium longum* subsp. *infantis* BLI-02 strains.

This indicates that the mixed fermentation products create a synergistic effect on the increasing of the stool water content. As above, the fermentation powders of lactic acid bacteria obtained in Example 2 can unexpectedly increase the stool water content.

It is noted that fermentation powders of lactic acid bacteria are a mixture of lactic acid bacterial metabolites and their function on the human health is attributed to the specificity of their nutrient ingredients, not lactic acid bacterial bodies. Since this kind of metabolites has benefit on human health, they are called as "postbiotics" (Trends in Food Science & Technology. 2018-05, 75: 105-114). Generally, the reaction of human and postbiotics is determined bacterial species, cultivation procedure, processing procedure, and clinical reports. For example, the paper published in International Journal of Molecular Sciences 2019, 20(19), 4673 points out that certain well-known treatment methods, such as heat sealing, physically treating, high hydrostatic pressure processing, lyophilization, or sonication lysis, can provide postbiotics the effect on human health, but the other treatment methods can't do so.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A method for improving constipation, comprising:
    administering a composition to a subject in need thereof so as to provide synergistic effect on a stool water content increase with the subject;
    wherein the composition comprises: a fermentation powder of lactic acid bacteria; and a physiologically acceptable excipient, diluent, or carrier;
    wherein the fermentation powder comprises: a fermentation product of lactic acid bacteria, and the fermentation product is a fermented supernatant of a culture medium containing inactivated strains, a fermented supernatant of a culture medium free of strains, or a powder thereof;
    wherein the fermentation product is obtained by incubating lactic acid bacterial strains in a culture medium containing milk, milk powders, casein, soy beans, bean products, or whey, then performing centrifugation on the culture medium to obtain a fermentation liquid, and then inactivating the strains in the fermentation liquid or filtering out the strains in the fermentation liquid;
    wherein the lactic acid bacterial strains comprise: a *Lactobacillus salivarius* subsp. *salicinius* AP-32 strain, a *Lactobacillus plantarum* LPL28 strain, a *Lactobacillus acidophilus* TYCA06 strain, and a *Bifidobacterium longum* subsp. *infantis* BLI-02 strain;
    wherein the *Lactobacillus salivarius* subsp. *salicinius* AP-32 strain is deposited at the China Center for Type Culture Collection (CCTCC) under an accession number CCTCC M2011127, the *Lactobacillus plantarum* LPL28 strain is deposited at the China General Microbiological Culture Collection Center (CGMCC) under an accession number CGMCC 17954, the *Lactobacillus acidophilus* TYCA06 strain is deposited at the China General Microbiological Culture Collection Center under an accession number CGMCC 15210, and the *Bifidobacterium longum* subsp. *infantis* BLI-02 strain is deposited at the China General Microbiological Culture Collection Center under an accession number CGMCC 15212.

2. The method as claimed in claim 1, wherein a symptom of the constipation comprises: formation of hard dry stools, a decrease in stool amount, difficulty in defecating, feeling incomplete bowel movement, or a decrease in defecating frequency.

3. The method as claimed in claim 2, wherein based on total weight of the composition, the fermentation product is present in 2-40% by weight.

4. The method as claimed in claim 2, wherein the composition further comprises: prebiotics.

5. The method as claimed in claim 1, wherein the lactic acid bacterial strains consist of the *Lactobacillus salivarius* subsp. *salicinius* AP-32 strain, the *Lactobacillus plantarum* LPL28 strain, the *Lactobacillus acidophilus* TYCA06 strain, and the *Bifidobacterium longum* subsp. *infantis* BLI-02 strain.

6. The method as claimed in claim 1, wherein the composition is a food composition or a pharmaceutical composition.

7. The method as claimed in claim 1, wherein the composition is a food composition, the physiologically acceptable excipient, diluent, or carrier is edible; and wherein the food composition is fermented milk drink, yogurt, cheese, powders of a milk product, tea, coffee, or energy drink.

8. The method as claimed in claim 1, wherein the composition is a pharmaceutical composition, the physiologically acceptable excipient, diluent, or carrier is pharmaceutically acceptable; and wherein the pharmaceutical composition is in tablet form, capsule form, powder form, cream form, spray form, gel form, solution form, or dispersant form.

9. The method as claimed in claim 1, wherein based on total weight of the composition, the fermentation product is present in 2-40% by weight.

10. The method as claimed in claim 1, wherein the composition further comprises: prebiotics.

* * * * *